United States Patent [19]
Okamoto et al.

[11] 3,989,733
[45] Nov. 2, 1976

[54] PROCESS FOR THE PREPARATION OF CYCLIC POLYDIORGANOSILOXANES
[75] Inventors: Haruo Okamoto; Isao Yanagisawa, both of Annnaka, Japan
[73] Assignee: Shinetsu Chemical Company, Tokyo, Japan
[22] Filed: Dec. 28, 1973
[21] Appl. No.: 429,272

[30] Foreign Application Priority Data
Dec. 30, 1972 Japan................................. 48-3123

[52] U.S. Cl........................................... 260/448.2 E
[51] Int. Cl.² ........................................... C07F 7/08
[58] Field of Search ............................. 260/448.2 E

[56] References Cited
UNITED STATES PATENTS
3,484,469  12/1969  Guinet et al. ................ 260/448.2 E
3,558,681  1/1971  Kuznetsova et al. ......... 260/448.2 E
3,607,898  9/1971  Macher......................... 260/448.2 E Primary Examiner—Paul F. Shaver
Attorney, Agent, or Firm—Toren, McGeady and Stanger

[57] ABSTRACT

Cyclic polydiorganosiloxanes, in particular, cyclic trisiloxanes are continuously prepared from mixed polydiorganosiloxane, the starting material, by subjecting them to thermal cracking and rectification in a reactor composed of a column, vertically held, comprising a catalyst zone at the lower part in which the thermal cracking takes place to produce cyclic polydiorganosiloxanes and a rectification zone at the upper part in which the cyclic polydiorganosiloxanes are rectified into several fractions and a still positioned below the column. The cyclic polydiorganosiloxanes have structures different from the starting polydiorganosiloxanes.

11 Claims, 1 Drawing Figure

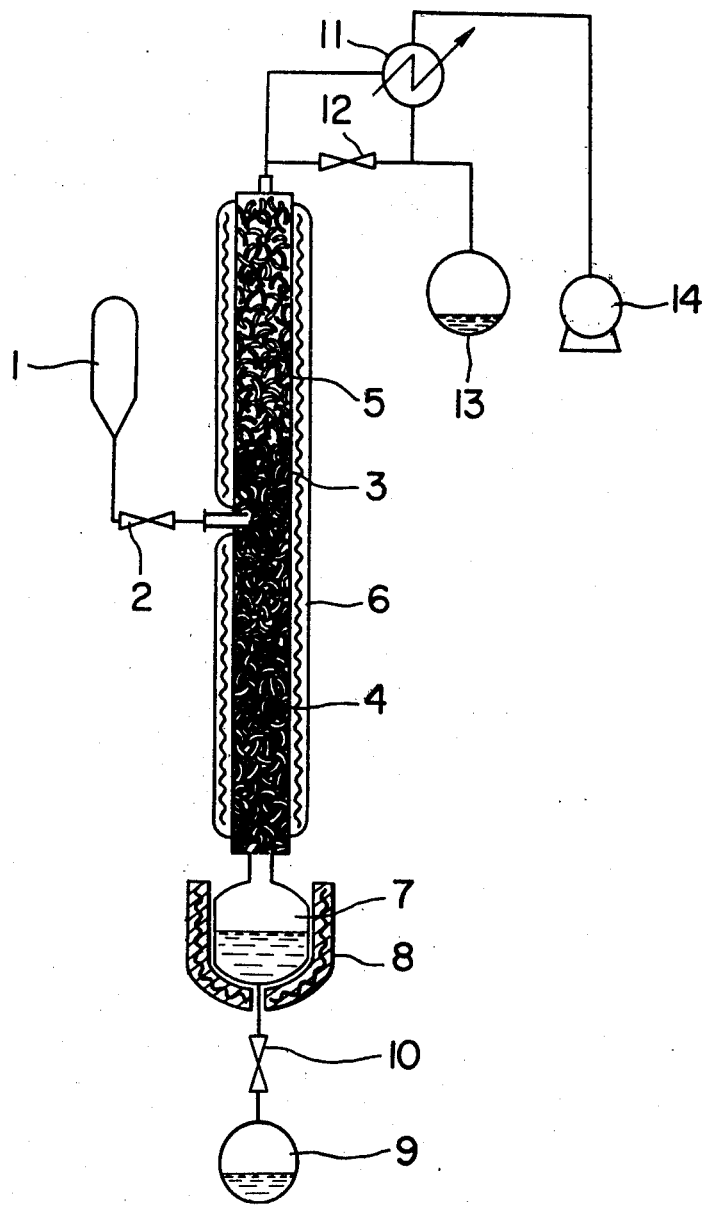

PROCESS FOR THE PREPARATION OF CYCLIC POLYDIORGANOSILOXANES

FIELD OF THE INVENTION

This invention relates to a process for the preparation of cyclic polydiorganosiloxanes, in particular, cyclic trimers of diorganosiloxanes. Cyclic polydiorganosiloxanes are important materials as the intermediates for the manufacture of various silicone products such as silicone fluids, rubbers and varnishes.

DESCRIPTION OF THE PRIOR ART

Several processes are known for the preparation of the cyclic polydiorganosiloxanes. Their examples are (a) hydrolyzates of an organochlorosilane are thermally cracked at high temperatures under high pressure in the presence of a hydroxide or carbonate of an alkali metal, such as lithium, sodium, potassium or cesium, with following distillation of the reaction mixture; (b) mixed diorganosiloxanes, dissolved in an inert organic solvent, are thermally cracked in the presence of a hydroxide of an alkali metal or an alkali silanolate as the catalyst, as described in Japanese patent publication No. 2149/1958; (c) hydrolyzates of phenyl methyl dichlorosilane are heated under reduced pressure in the presence of a carbonate of an alkali metal to yield 1,3,5,7-tetramethyl-1,3,5,7-tetraphenyl cyclotetrasiloxane, as described in U.S. Pat. No. 3,484,469; and (d) phenyl methyl dichlorosilane or phenyl methyl dialkoxysilane is hydrolyzed and the resulting hydrolyzates are subjected to condensation reaction, and the resulted polysiloxane are thermally cracked in the presence of lithium hydroxide or lithium silanolate as the catalyst, as described in Japanese patent publication No. 34118/1971.

These conventional processes have many disadvantages. For example, the efficiency of the method (a) in commercial production is low because it is a batch-wise process and the reaction product must be subjected to distillation to give pure fractions of the individual cyclic polysiloxanes; the reaction product of the method (b) contains a large amount of high-boiling viscous materials and the cyclic trisiloxanes cannot be obtained in high yield; and the yields of the cyclic polydiorganosiloxanes in the methods (c) and (d) are low and, in addition, the cyclic siloxanes by these methods are rich in cyclic tetramers with correspondingly very low contents of the desired trimers.

SUMMARY OF THE INVENTION

The present invention provides an improved process, free of the above-described disadvantages, for the preparation of cyclic polydiorganosiloxanes.

The object of the present invention is to convert linear polydiorganosiloxanes into cyclic polydiorganosiloxanes.

It is another object of the invention to convert cyclic polydiorganosiloxanes, e.g., cyclic tetrasiloxanes into other cyclic polydiorganosiloxanes containing a different number of diorganosiloxane units, e.g., cyclic trisiloxanes.

In the preparation of cyclic polydiorganosiloxanes according to the method of the invention, there is used a reactor composed of a column comprising two separate portions, the lower half being a catalyst zone and the upper half being a rectification zone and a still positioned below and connected to the column. Mixed polydiorganosiloxanes as the raw material are continuously fed to the catalyst zone, therein to be thermally cracked, and rectified in the rectification zone, so that the thermal cracking and rectification take place continuously, to finally produce pure fractions of desired cyclic polydiorganosiloxanes having structures different from the raw material polydiorganosiloxanes, while simultaneously recovering the product from the reaction column.

The present invention is based on the discovery that cyclic polydiorganosiloxanes having structures different from those of the raw material siloxanes, or, in particular, cyclic diorganosiloxane trimers can be obtained continuously in high yield through the thermal cracking and rectification processes by use of the reactor column, comprising the catalyst and rectification zones, with a still connected thereto.

The raw material polysiloxanes fed to the catalyst zone undergo cracking rearrangement in the course of flowing down through the catalyst zone, forming the desired cyclic polysiloxanes to the equilibrium concentration with any unreacted raw material polysiloxanes within the liquid layer on the catalyst surface. The cyclic polysiloxanes thus formed move into the vapors of the cyclic polysiloxanes ascending in the reactor column. The efficiency of the cracking reaction is very high because the unreacted raw material polysiloxanes are always in contact with the catalyst surfaces and the cyclic polysiloxanes formed by the thermal cracking with the layer of the unreacted polysiloxanes on the catalyst surfaces rapidly move into the vapor phase through the interface, thus giving rise to a shift of the equilibrium state toward the favorable direction.

The temperature of the catalyst zone can be optimized by regulating the input of the heating element provided around the reactor column.

In the prior art, the raw material polysiloxanes can be heated together with the catalyst in a reactor vessel equipped with a stirrer. In this case, the reaction of the cracking rearrangement does not proceed as completely in the direction favored by the chemical equilibrium. In the case where the equilibrium concentration of the desired cyclic polysiloxanes is very low, the preparation of the cyclic polysiloxanes by this method is practically impossible. On the contrary, the method of the present invention can be carried out very efficiently for the preparation of the cyclic trisiloxanes which have a very low equilibrium concentration even at high temperatures.

The process of the present invention will be described with reference to the accompanying drawing, showing a schematic illustration of the apparatus employed.

In the drawing, 1 is a feeder tank for raw material; 2 is a regulation valve for the feeding of raw material; 3 is a reactor column made of a heat-resistant material, such as, Pyrex glass or stainless steel; the lower part 4 of reactor column 3 is a catalyst zone packed with pellets of a hydroxide or carbonate of an alkali metal or a packing such as McMahon packing or Raschig rings with a layer of the hydroxide or carbonate of an alkali metal fused at 600° – 900° C, adhered on its surface; the upper part 5 of reactor column 3 is a rectification zone packed with a packing, such as, McMahon packing, Raschig ring or Stedman packing; 6 is a heater element surrounding reactor column 3, which serves to heat the catalyst zone to an appropriate reaction temperature and, at the same time, to prevent the lowering of the rectifying efficiency due to heat dissipation from the rectification zone; 7 is a still connected to the bottom of reactor column 3; 8 is a heater to heat still 7; 9 is a receiver connected to the bottom of still 7 through a valve 10; 11 is a condenser connected to the top of reactor column 3; 12 is a valve; 13 is a receiver into which the product is recovered, and 14 is a vacuum pump.

In a preferred embodiment of the cyclic polydiorganosiloxane producing process of the present invention, the raw material, mixed polydiorganosiloxanes or together with a solvent, stored in feeder tank 1 is continuously introduced through regulation valve 2 into catalyst zone 4, to be thermally cracked therein. Vapors of the mixed siloxanes containing the resulting cyclic polysiloxanes ascend in reactor column 3 while any unreacted high-boiling siloxanes flow downward in the column. The unreacted siloxanes are subjected to thermal cracking again during the downward movement, to form the desired cyclic polysiloxanes. These reactions and movements are repeated, and yet any unreacted siloxanes tend to drop into still 7. Such siloxanes having a boiling point close to that of the cyclic polysiloxanes and the solvent remaining in still 7 are partly evaporated by heat by heater 8 and ascend into reactor column 3, while any superfluous volumes of the solvent containing the unreacted material are extracted from the still to receiver 9 continuously or intermittently under control by valve 10. The unreacted material and solvent containing solution may be used again as the raw material. In some cases, a small amount of a hydroxide or carbonate of an alkali metal may be put into still 7 so that the thermal cracking reaction takes place also in the still. The cyclic polysiloxanes in vapor form ascending through the reactor column 3 and having entered rectification zone 5 are rectified into separate, pure fractions of the individual cyclic polysiloxanes, and the vapors of the rectified cyclic polydiorganosiloxane are introduced into condenser 11 for condensation. Part of the condensate is recovered into receiver 13 while the remainder is refluxed back to reactor column 3 through valve 12 for contact with the ascending vapors in the reactor column.

If the raw material siloxane has a high boiling point as in the case of methyl phenyl polysiloxane, it is preferred that the process should be carried out under a pressure reduced by means of vacuum pump 14.

A wide variety of polydiorganosiloxanes can be used as the raw material for the process of the present invention. They include linear polydiorganosiloxanes like polydimethylsiloxane and methyl phenyl polysiloxane, as well as hydrolyzates of diorganodichlorosilanes, such as dimethyldichlorosilane, methyl phenyl dichlorosilane, methyl vinyl dichlorosilane and trifluoromethyl methyl dichlorosilane, such hydrolyzates being a mixture of linear polysiloxanes and cyclic polysiloxanes. Of course, a mere mixture of linear polysiloxanes and cyclic polysiloxanes can be employed. When a cyclic trisiloxane is to be prepared, the corresponding cyclic tetrasiloxane or pentasiloxane will be a favorable raw material. Other suitable examples include mixtures of polysiloxanes having different organic groups, such as mixtures of octamethylcyclotetrasiloxane and 1,3,5,7-tetramethyl-1,3,5,7-tetravinylcyclotetrasiloxane that will lead to the formation of the mixture of hexamethyl cyclotrisiloxane, 1-vinyl-1,3,3,5,5-pentamethyl cyclotrisiloxane, 1,3-divinyl-1,3,5,5-tetramethyl cyclotrisiloxane and 1,3,5-trivinyl-1,3,5-trimethyl cyclotrisiloxane.

Since the raw material polydiorganosiloxanes have a tendency to polymerize at high temperatures as in the case of methyl vinyl siloxanes, it is recommended that, in order to retard the polymerization reaction, a small amount of a solvent is admixed with the raw material before it is fed to the reaction column or is put into the reaction column prior to operation. The solvents suitable for the purpose should have a boiling point higher than that of the desired cyclic polysiloxane. They are exemplified by tetraethyleneglycol dimethyl ether, alkylnaphthalenes and high-boiling mineral oils.

The temperature at which the catalyst zone is heated is in the range from 100° to 300° C, depending on the kind of the cyclic polydiorganosiloxane to be produced.

The catalyst zone may be filled with alternate layers of lithium hydroxide pellets and, for example, the McMahon packing, thus bringing about the advantage of simultaneous performance of thermal cracking and rectification. The height of the reactor column should be determined according to kinds of the raw materials to be employed. Almost no weight loss of the catalyst bed is attained when the catalyst bed is composed of lithium hydroxide pellets and the McMahon packing is covered with a layer of fused lithium hydroxide.

The following examples are illustrative of the present invention and should not be construed as limiting the invention. Percentages are all by weight.

EXAMPLE 1

There was provided a reactor column made of Pyrex glass, 25 mm in inner diameter and 800 mm long, having an inleft for feeding raw material therethrough at about its middle, equipped with a still connected to its bottom and a condenser connected to its top. The column was filled with pellets of the McMahon packing, each 6 mm in diameter with a fused layer of lithium hydroxide adhered on its surface up to the height of about 500 mm from the bottom and with the same packing having no lithium hydroxide layer, thereabove up to the top.

The feeder tank was charged with 500 g of the raw material hydrolyzate of dimethyl dichlorosilane, from which cyclic siloxanes had been removed by distillation. Lithium hydroxide was not placed in the still. The raw material was continuously introduced into the reactor column through the inlet. The operation was conducted at atmospheric pressure with partial reflux of the condensate while maintaining the still at 240° C, the column just below the inlet at 200° C and the exit on the top of the column at 140° C. After 24 hours of the operation, a white crystalline product and liquid product containing a small amount of crystalline material were collected in the receiver. No residue was found in the still.

The crystalline product thus obtained was analyzed by gas chromatography and it was found that it contained 286 g of hexamethyl cyclotrisiloxane, 170 g of octamethyl cyclotetrasiloxane and 130 g of others.

EXAMPLE 2

The arrangement of the reactor was the same as in the preceding example except that the column was 15 mm in inner diameter and 600 mm long. The column was packed with pellets of the McMahon packing with fused lithium hydroxide layer up to the height of 400 mm from the bottom and with the same packing, having no lithium hydroxide layer, thereabove up to the top. The feeder tank was charged with 500 g of hydrolyzate of methyl phenyl dichlorosilane, from which water and low-boiling fractions had been removed by distillation under reduced pressure in advance. No lithium hydroxide was placed in the still. The operation was conducted under reduced pressure of 3 mmHg maintaining the temperature of the exit from the reactor column at 180° C and that of the reaction zone at 270° C.

After 8 hours of thermal cracking reaction, the reaction product was distilled under reduced pressure and rectified into separate fractions, and it was found that the reaction product contained, outside a small amount of the residue in the still, 285 g of the fraction up to 200° C/3 mmHg corresponding to 1,3,5-trimethyl-1,3,5-triphenyl cyclotrisiloxane, 210 g of the fraction up to 250° C/3 mmHg corresponding to 1,3,5,7-tetramethyl-1,3,5,7-tetraphenyl cyclotetrasiloxane and 5 g of the high-boiling residue.

EXAMPLE 3

The arrangement of the reaction apparatus was the same as in Example 1 except that lithium carbonate was employed in place of lithium hydroxide as the catalyst. The feeder tank was charged with a mixture of 500 g of 1,3,5,7-tetramethyl-1,3,5,7-tetravinyl cyclotetrasiloxane and 100 g of tetraethyleneglycol dimethyl ether. No lithium hydroxide or carbonate was placed in the still. The operation was conducted under reduced pressure of 20 mmHg with the temperatures of 150° C at the exit from the column, 170° C in the reaction zone and 180° C inside the still. After 8 hours of the thermal cracking reaction, 495 g of the reaction product was obtained and 98 g of tetraethyleneglycol dimethyl ether remained in the still.

The reaction product was analyzed by gas chromatography and it was found that the reaction product was composed of 15 % of 1,3,5-trimethyl-1,3,5-trivinyl cyclotrisiloxane and 85 % of 1,3,5,7-tetramethyl-1,3,5,7-tetravinyl cyclotetrasiloxane.

EXAMPLE 4

The reaction apparatus employed was the same as in Example 2. Pellets of lithium hydroxide 4 mm in average diameter and pellets of the McMahon packing 6 mm in diameter were packed in the reactor column in alternate layers up to the height of 400 mm from the bottom, and a bed of the same McMahon packing thereabove up to the top. The feeder tank was charged with hydrolyzate of methyl phenyl dichlorosilane, from which water and the low-boiling fractions had been removed by distillation under reduced pressure in advance. No lithium hydroxide was placed in the still. The operation was conducted under reduced pressure of 3 mmHg with the temperatures of 180° C at the top of the column and 270° C in the reaction zone.

After 8 hours of the thermal cracking reaction, the reaction product was rectified under reduced pressure into separate fractions. The fractions obtained were 219 g (43.8%) of the fraction up to 200° C/3 mmHg corresponding to 1,3,5-trimethyl-1,3,5-triphenyl cyclotrisiloxane, 209 g (41.8%) of the fraction up to 250° C/3 mmHg corresponding to 1,3,5,7-tetramethyl-1,3,5,7-tetraphenyl cyclotetrasiloxane and 72 g (14.4%) of high-boiling residue.

EXAMPLE 5

The reaction apparatus was the same as in Example 1 except that the reaction column was made of a stainless steel, 50 mm in inner diameter and 1,000 mm long. The reactor column was packed with lithium hydroxide pellets of the same size as in Example 4 and Raschig rings of 8 mm diameter in alternate layers to the height about 700 mm from the bottom, and a bed of the McMahon packings with 300 mm height was formed on the top of the alternate layers. No lithium hydroxide was placed in the still. The feeder tank was charged with 15 kg of mixed dimethylsiloxanes, obtained by the hydrolysis of dimethyl dichlorosilane, containing 50 % of cyclic siloxane including trace amount of hexamethyl cyclotrisiloxane. The operation was conducted under atmospheric pressure with the temperatures of 160° C at the exit from the column, 180° C in the reaction zone and 250° C inside the still.

After 6 hours of the thermal cracking reaction, 14.8 kg of the reaction product was obtained which was composed of 8 % of hexamethyl cyclotrisiloxane, 60 % of octamethyl cyclotetrasiloxane and 32 % of decamethyl cyclopentasiloxane by gas chromatographic data.

EXAMPLE 6.

The reaction apparatus and the raw material were the same as in Example 5. The feeder tank was charged with 16 kg of the mixed dimethylsiloxanes. No lithium hydroxide was placed in the still. The operation was conducted under atmospheric pressure with the temperatures 150° to 170° C at the top of the column, 200° C in the reaction zone and 250° C inside the still.

After about 8 hours of the thermal cracking reaction, 15.5 kg of the reaction product was obtained, which was composed of 15 % of hexamethyl cyclotrisiloxane, 55 % of octamethyl cyclotetrasiloxane and 30 % of decamethyl cyclopentasiloxane.

EXAMPLE 7

The reaction apparatus employed was the same as in Example 1. The raw material charged into the feeder tank was 240 g of the hydrolyzate of dimethyl dichlorosilane containing 45 % of the low-boiling fractions including about 1 % of hexamethyl cyclotrisiloxane. No lithium hydroxide was placed in the still. The operation was conducted under reduced pressure of 100 mmHg with the temperatures 170° C in the reaction zone and 250° C inside the still under partial reflux of the distillate. The results obtained after 3.5 hours of the thermal cracking reaction are shown in the table below along with the comparative data obtained by the control examples to follow.

Control 1

Into a 1 liter distillation flask, 500 g of the same hydrolyzate as employed in Example 7 as the raw material and 0.5%, based on the hydrolyzate, of powdered lithium hydroxide were charged. Thermal cracking reaction was carried out by heating under reduced pressure of 100 mmHg with partial reflux of the distillate for 5 hours. The results are shown in the table.

Control 2

Powdered potassium hydroxide was employed in place of lithium hydroxide. The operation conditions were the same as in Control 1. The results are shown in the table.

TABLE

|  | Example 7 | Control 1 | Control 2 |
|---|---|---|---|
| Temperature in the reaction zone | 170° C | — | — |
| Temperature inside the still | 250° C | 300° C | 293° C |
| Distillate/raw material | 97 % | 91 % | 85 % |
| Hexamethyl cyclotrisiloxane | 22 % | 7 % | 5 % |
| Octamethyl cyclotetrasiloxane | 53 % | 50 % | 59 % |
| Decamethyl cyclopentasiloxane | 20 % | 35 % | 30 % |
| Dodecamethyl cyclohexasiloxane | 5 % | 8 % | 6 % |

EXAMPLE 8

The reaction apparatus employed was the same as in Example 2. The feeder tank was charged with 500 g of hydrolyzate of dimethyl dichlorosilane, while the still was charged with 200 g of the same material and 7 g of lithium hydroxide. The operation was conducted under atmospheric pressure with partial reflux of the condensate while maintaining the inside of the still at 240° C and the reaction zone at 200° C and the top of the column at 140° C. This operation was completed in 6 hours, to produce 690 g of mixed siloxanes. The product was then analyzed by gas chromatography to find that 55% being hexamethyl cyclotrisiloxane and the remaining 45% being octamethyl cyclotetrasiloxane and other cyclic siloxanes.

EXAMPLE 9

The same reaction apparatus as in Example 2 was employed. The reaction zone was charged with granular potassium hydroxide and the McMahon packing in alternative layers, while the feed tank was charged with 500 g of hydrolyzate of trifluoromethylmethyldichlorosilane and the still with 200 g of the same hydrolyzate (but, without potassium hydroxide). The Operation was conducted under reduced pressure of 30 mmHg with partial reflux of the condensate, while maintaining the reaction zone at 180° C and the inside of the still at 200° C. This operation was completed in 5 hours, to produce 650 g of mixed siloxanes. The product was analyzed by gas chromatography to find that 60% was 1,3,5-tri(trifluoromethyl)-1,3,5-trimethyl cyclotrisiloxane and the remaining 40% was 1,3,5,7-tetra(trifluoromethyl)-1,3,5,7-tetramethyl cyclotetrasiloxane.

What is claimed is:

1. In a process for the thermal cracking of polydiorganosiloxanes in the presence of an alkaline catalyst to produce cyclic polydiorganosiloxanes, the improvement which comprises carrying out the reaction using the following steps:

a. introducing the starting polydiorganosiloxane into the upper portion of the catalytic zone of a vertical reaction column;
   b. thermally cracking the starting polydiorganosiloxane within the catalytic zone to produce vapors of a cyclic polydiorganosiloxane;
   c. discharging any unreacted material to a still in communication with the bottom of the reaction column;
   d. rectifying the vapors in a rectification zone in communication with the top of the catalytic zone; and
   e. removing the rectified cyclic polydiorganosiloxane from the top of the rectification zone.

2. The process as claimed in claim 1 wherein said catalytic zone is packed with a granular hydroxide of an alkali metal or a packing material having a fused layer of hydroxide of an alkali metal adhered to its surface.

3. The process as claimed in claim 1 wherein said catalytic zone is packed with a granular carbonate of an alkali metal or a packing material having a fused layer of carbonate of an alkali metal adhered to its surface.

4. The process as claimed in claim 1 wherein said catalytic zone is packed with alternate layers of a granular hydroxide or carbonate of an alkali metal and a packing material.

5. The process as claimed in claim 4 wherein said packing material is covered with a fused layer of a hydroxide or carbonate of an alkali metal.

6. The process as claimed in claim 1 wherein said rectification zone is packed with a material selected from the group consisting of McMahon packing, Raschig rings and Stedman packing.

7. The process as claimed in claim 1 wherein said catalytic zone is heated to a temperature in the range from 100° to 300° C.

8. The process as claimed in claim 1 wherein lithium hydroxide or a carbonate of an alkali metal is placed in said still.

9. The process as claimed in claim 1 wherein said raw material polydiorganosiloxane is selected from the group consisting of the hydrolyzates of halogen substituted or unsubstituted diorganodichlorosilanes and mixtures thereof.

10. The process as claimed in claim 1 wherein said raw material polydiorganosiloxane is diluted with a solvent having a boiling point higher than that of said cyclic polydiorganosiloxane.

11. The process of claim 1 which comprises thermally cracking raw material polysiloxane selected from the group consisting of linear polydiorganosiloxanes and cyclic polydiorganosiloxanes having a degree of polymerization higher than 3, to produce hexaorganocyclotrisiloxane and subjecting said hexaorganocyclotrisiloxane to rectification in the rectification zone.

* * * * *